United States Patent
Berchtold

(10) Patent No.: US 7,193,035 B2
(45) Date of Patent: Mar. 20, 2007

(54) CRYSTALS OF INSULIN ANALOGS AND PROCESSES FOR THEIR PREPARATION

(75) Inventor: Harald Berchtold, Kronberg (DE)

(73) Assignee: Sanofi-Aventis Deutschland GmbH, Frankfurt (DE)

(*) Notice: Subject to any disclaimer, the term of this patent is extended or adjusted under 35 U.S.C. 154(b) by 304 days.

(21) Appl. No.: 10/696,011

(22) Filed: Oct. 29, 2003

(65) Prior Publication Data

US 2005/0085621 A1 Apr. 21, 2005

Related U.S. Application Data

(60) Provisional application No. 60/451,862, filed on Mar. 4, 2003.

(30) Foreign Application Priority Data

Oct. 29, 2002 (DE) ............................ 102 50 297

(51) Int. Cl.
*A61K 38/28* (2006.01)
(52) U.S. Cl. .................................................. 530/303
(58) Field of Classification Search ................ 530/303
See application file for complete search history.

(56) References Cited

U.S. PATENT DOCUMENTS

| | | | |
|---|---|---|---|
| 4,644,057 A | 2/1987 | Bicker et al. | |
| 5,101,013 A | 3/1992 | Dorschug et al. | |
| 5,358,857 A | 10/1994 | Stengelin et al. | |
| 5,473,049 A | 12/1995 | Obermeier et al. | |
| 5,663,291 A | 9/1997 | Obermeier et al. | |
| 6,221,633 B1 * | 4/2001 | Ertl et al. | 435/69.4 |
| 6,310,038 B1 * | 10/2001 | Havelund | 514/4 |
| 6,818,738 B2 * | 11/2004 | Havelund | 530/303 |

FOREIGN PATENT DOCUMENTS

| | | |
|---|---|---|
| EP | 0 214 826 | 3/1987 |
| EP | 0 375 437 | 6/1990 |
| EP | 0 419 504 | 4/1991 |
| EP | 0 678 522 | 10/1995 |
| EP | 0709395 | 5/1996 |
| WO | WO 98/42749 | 10/1998 |
| WO | WO 02/076495 | 10/2002 |

OTHER PUBLICATIONS

Giege et al. Crystallogenesis of Biological Macromolecules: Facts and Perspectives. Acta Cryst., (1994) D50. pp. 339-350.*
Wittingham et al. X-ray Crystallographic Studies on Hexameric Insulins in the Presence of Helix-Stabilizing Agents, Thiocyanate, Methlyparaben, and Phenol. Biochemistry. 1995. vol. 34, pp. 15553-15563.*
Drenth, J. "Principles of Protein X-Ray Crystallography", 2nd Edition, 1999 Springer-Verlag New York Inc., Chapter 1, pp. 1-19.*
Weber, P.C. Overview of Protein Crystallization Methods. Methods in Enzymology, 1997, vol. 276, pp. 13-22.*
Baker, E.N., et. al., The Structure Of 2Zn Pig Insulin Crystals At 1.5 A Resolution, Phil. Trans. R. Soc. Land, (1998), vol. 319, pp. 369-456.
Bentley, G.A., et. al., Role Of B13 Glu In Insulin Assembly; The Hexamer Structure Of Recombinant Mutant (B13 Glu Gln) Insulin, Journal Of Molecular Biology, (1992), vol. 228, pp. 1163-1176.
Berger M., et. al., Towards More Physiological Insulin Therapy In the 1990s, Diabetes Research and Clinical Practice, (1989), vol. 6, pp. S25-S31.
Bernstein, F.C., et. al., The Protein Data Bank: A Computer-Based Archival File For Macromolecular Structures, Journal Of Molecular Biology, (1977), vol. 112, pp. 535-542.
Bolli, G.B., et. al., The Pharmacokinetic Basis Of Insulin Therapy In Diabetes Mellitus, Diabetes Research and Clinical Practice, (1989), vol. 6, pp. S3-S16.
Brange, J., et. al., Neutral Insulin Solutions Physically Stabilized By Addition Of Zn2+, Diabetic Medicine, (1986), vol. 3, pp. 532-536.
Dixon, G.H., et. al., Regeneration Of Insulin Activity From The Separated And Inactive A and B Chains, Nature, (1960), vol. 188, No. 4752, pp. 721-724.
Drury, P.L., et. al., Diabetic Nephropathy, British Medical Bulletin, (1989), vol. 45, No. 1, pp. 127-147.
Home, P.D., et. al., Insulin Treatment: A Decade Of Change, British Medical Bulletin, (1989), vol. 45, No. 1, pp. 92-110.
Kang, S., et. al., Subcutaneous Insulin Absorption Explained By Insulin's Physicochemical Properties Evidence From Absorption Studies Of Soluble Human Insulin And Insulin Analogues in Humans, Diabetes Care, (1991), vol. 14, No. 11, pp. 942-948.
Kemmler, W., et. al., Studies On The Conversion Of Proinsulin To Insulin, The Journal Of Biological Chemistry, (1971), vol. 246, No. 22, pp. 6786-6791.
Kohner, E.M., et. al., Diabetic Retinopathy, British Medical Bulletin, (1989), vol. 45, No. 1, pp. 148-173.
Marshall, R.C., et. al., Protein Oligomer Composition, Preparation of Monomers and Constituent Chains, Practical Protein Chemistry—A Handbook (1986) S. 49-53.
The Diabetes Control And Complications Trial Research Group, The Effect Of Intensive Treatment Of Diabetes On The Development And Progression Of Long-Term Complications In Insulin-Dependent Diabetes Mellitus, The New England Journal Of Medicine, (1993), vol. 218, No. 14, pp. 977-986.
Ward, J.D., et. al., Diabetic Neuropathy, British Medical Bulletin, (1989), vol. 45, No. 1, pp. 111-126.

* cited by examiner

*Primary Examiner*—David J. Steadman
*Assistant Examiner*—Suzanne M. Noakes
(74) *Attorney, Agent, or Firm*—Mark C. Nelligan

(57) ABSTRACT

The invention relates to crystals of an insulin analog in which asparagine (Asn) in position B3 of the B chain is replaced by a naturally occurring basic amino acid residue and at least one amino acid residue in the positions B27, B28 or B29 of the B chain is replaced by another naturally occurring neutral or acidic amino acid residue, where phenylalanine (Phe) in position B1 of the B chain can optionally be absent, the crystals being present in the space group R3 (No. 146) with the cell axes A=81.5 Å±1 Å and C=33.3 Å±1 Å, their preparation and use, and a pharmaceutical composition comprising these crystals.

13 Claims, No Drawings

CRYSTALS OF INSULIN ANALOGS AND PROCESSES FOR THEIR PREPARATION

FIELD OF THE INVENTION

The invention relates to crystals of an insulin analog in which asparagine (Asn) in position B3 of the B chain is replaced by a naturally occurring basic amino acid residue and at least one amino acid residue in the positions B27, B28 or B29 of the B chain is replaced by another naturally occurring neutral or acidic amino acid residue, where phenylalanine (Phe) in position B1 of the B chain can optionally be absent, the crystals being present in the space group R3 (No. 146) with the cell axes A=81.5 Å±1 Å and C=33.3 Å±1 Å.

BACKGROUND OF THE INVENTION

Worldwide, approximately 120 million people suffer from diabetes mellitus. Among these, approximately 12 million are type I diabetics, for whom the administration of insulin is the only therapy currently possible. The people affected have a lifelong dependence on insulin injections, as a rule several times per day. Although type 11 diabetes, from which approximately 100 million people suffer, is not in principle accompanied by a lack of insulin, in a large number of cases treatment with insulin is regarded as the most favorable or only possible form of therapy.

With progressing duration of the illness, a large number of the patients suffer from "diabetic late complications". What is involved here is essentially micro- and macrovascular damage, which depending on the type and extent results in kidney failure, blindness, loss of extremities or an increased risk of cardiovascular diseases.

As a cause, chronically raised blood glucose levels have primarily been held responsible, since even with careful adjustment of the insulin therapy a normal blood glucose profile, as would correspond to physiological regulation, is not achieved (Ward, J. D. (1989) British Medical Bulletin 45, 111–126; Drury, P. L. et al. (1989) British Medical Bulletin 45, 127–147; Kohner, E. M. (1989) British Medical Bulletin 45, 148–173).

In the healthy person, the insulin secretion is closely dependent on the glucose concentration of the blood. Raised glucose levels, as occur after meals, are rapidly compensated by increased release of insulin. In the fasting state, the plasma insulin level falls to a basal value, which suffices to guarantee a continuous supply of insulin-sensitive organs and tissue with glucose. An optimization of the therapy, "intensified insulin therapy", is today primarily aimed at keeping variations of the blood glucose concentration, especially upward deviations, as low as possible (Bolli, G. B. (1989) Diabetes Res. Clin. Pract. 6, P3–P16; Berger, M. (1989) Diabetes Res. Clin. Pract. 6, P25–P32). This leads to a significant decrease in the occurrence and the progress of diabetic late damage (The Diabetes Control and Complications Trial Research Group (1993) N. Engl. J. Med. 329, 977–986).

From the physiology of insulin secretion, it can be deduced that for an improved, intensified insulin therapy using subcutaneously administered preparations, two insulin preparations having different pharmacodynamics are needed. For the compensation of the blood glucose increase after meals, the insulin must flow in rapidly and may only act for a few hours. For the basal supply, in particular in the night, a preparation should be available which acts for a long time, has no pronounced maximum and only flows in very slowly.

The preparations based on human and animal insulins fulfill the claims of an intensified insulin therapy, however, only to a restricted extent. Rapidly active insulins (old insulins) reach the blood and the site of action too slowly and have an excessively long total duration of action. The result is that the postprandial glucose levels are too high and several hours after the meal the blood glucose falls too far (Kang, S. et al. (1991) Diabetes Care 14, 142–148; Home, P. J. et al. (1989) British Medical Bulletin 45, 92–110; Bolli, G. B. (1989) Diabetes Res. Clin. Pract. 6, P3–P16). The available basal insulins in turn, especially NPH insulins, have too short a duration of action and possess an excessively strongly pronounced maximum.

In addition to the possibility of influencing the profile of action by means of pharmaceutical principles, the aid of genetic engineering today offers the alternative of designing insulin analogs which achieve certain properties such as onset and duration of action on their own due to their structural properties. By means of the use of suitable insulin analogs, an adjustment of the blood glucose which is significantly better and adapted more closely to the natural conditions could therefore be achieved.

Insulin analogs having an accelerated onset of action are described in EP 0 214 826, EP 0 375 437 and EP 0 678 522. EP 0 214 826 relates, inter alia, to substitutions of B27 and B28, but not in combination with the substitution of B3. EP 0 678 522 describes insulin analogs which contain various amino acids, preferably proline, in position B29, but not glutamic acid. EP 0 375 437 comprises insulin analogs having lysine or arginine in B28, which can optionally additionally be modified in B3 and/or A21. In EP 0 885 961 A1, B3-lysine, B29-glutamate human insulin is disclosed as a novel, rapidly acting insulin.

In EP 0 419 504, insulin analogs are disclosed which are protected against chemical modifications by changing asparagine in B3 and at least one further amino acid in the positions A5, A15, A18 or A21. The insulin analogs described here, however, have only one modification in the position B3 and no further modification of the group mentioned. There is no indication that these compounds possess changed pharmacodynamics with the consequence of a more rapid onset of action.

Insulin analogs are analogs of naturally occurring insulins, namely human insulin or animal insulins, which differ by substitution of at least one naturally occurring amino acid residue and/or addition of at least one amino acid residue and/or organic residue of the corresponding, otherwise identical naturally occurring insulin.

The A chain of human insulin has the following amino acid sequence: Gly Ile Val Glu Gln Cys Cys Thr Ser Ile Cys Ser Leu Tyr Gln Leu Glu Asn Tyr Cys Asn (SEQ ID NO 1)

The B chain of human insulin has the following amino acid sequence: Phe Val Asn Gln His Leu Cys Gly Ser His Leu Val Glu Ala Leu Tyr Leu Val Cys Gly Glu Arg Gly Phe Phe Tyr Thr Pro Lys Thr (SEQ ID NO 2).

BRIEF SUMMARY OF THE INVENTION

The crystals of the insulin analogs of the present invention contain an insulin analog or a physiologically tolerable salt thereof, in which asparagine (Asn) in position B3 of the B chain is replaced by a naturally occurring basic amino acid residue and at least one amino acid residue in the positions B27, B28 or B29 of the B chain is replaced by another naturally occurring amino acid residue, where phenylalanine (Phe) in position B1 of the B chain can optionally be absent.

Preferably, the insulin analog or its physiologically tolerable salt is characterized by formula I

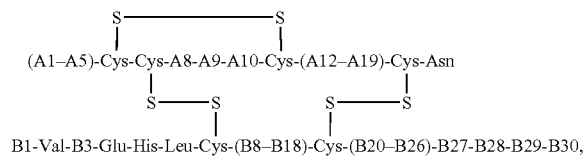

in which
(A1–A5) are the amino acid residues in the positions A1 to A5 of the A chain of human insulin (cf. SEQ ID NO 1) or animal insulin,
(A8–A10) are the amino acid residues in the positions A8 A9 and A10 of the A chain of human insulin (cf. SEQ ID NO 1) or animal insulin,
(A12–A19) are the amino acid residues in the positions A12 to A19 of the A chain of human insulin (cf. SEQ ID NO 1) or animal insulin,
(B8–B18) are the amino acid residues in the positions B8 to B18 of the B chain of human insulin (cf. SEQ ID NO 2) or animal insulin,
(B20–B26) are the amino acid residues in the positions B20 to B26 of the B chain of human insulin (cf. SEQ ID NO 2) or animal insulin,
(B30) is the amino acid residue in position B30 of the B chain of human insulin (cf. SEQ ID NO 2) or animal insulin,
B1 is a phenylalanine residue (Phe) or a hydrogen atom,
B3 is a naturally occurring basic amino acid residue,
B27, B28
and B29 are the amino acid residues in the positions B27, B28 and B29 of the B chain of human insulin (cf. SEQ ID NO 2) or animal insulin or in each case another naturally occurring amino acid residue, where at least one of the amino acid residues in the positions B27, B28 and B29 of the B chain is replaced by another naturally occurring amino acid residue.

DETAILED DESCRIPTION OF THE INVENTION

Of the twenty naturally occurring amino acids which are genetically encodable, the amino acids glycine (Gly), alanine (Ala), valine (Val), leucine (Leu), isoleucine (Ile), serine (Ser), threonine (Thr), cysteine (Cys), methionine (Met), asparagine (Asn), glutamine (Gln), phenylalanine (Phe), tyrosine (Tyr), tryptophan (Trp) and proline (Pro) are designated as neutral amino acids, the amino acids arginine (Arg), lysine (Lys), and histidine (His) are designated as basic amino acids and the amino acids aspartic acid (Asp) and glutamic acid (Glu) are designated as acidic amino acids.

Preferably, the crystals of the insulin analogs of the present invention contain an insulin analog of bovine insulin, porcine insulin, ovine insulin or human insulin or its physiologically tolerable salt, namely an insulin analog or a physiologically tolerable salt of the formula I, which is distinguished in that A8 is alanine (Ala),
A9 is serine (Ser),
A10 is valine (Val) and
B30 is alanine (Ala) (amino acid residues A8 to A10 and B30 of bovine insulin),
A8 is threonine (Thr),
A9 is serine (Ser) and
A10 is isoleucine (Ile) (amino acid residues A8 to A10 of the insulins of humans or pigs), where
B30 is alanine (Ala) (amino acid residue B30 of porcine insulin) or
B30 is threonine (Thr) (amino acid residue B30 of human insulin, cf. SEQ ID NO 2).

An insulin analog or a physiologically tolerable salt thereof of the formula I with the amino acid residues A8 to A10 and B30 of human insulin is particularly preferred, which is further distinguished in that
(A1–A5) are the amino acid residues in the positions A1 to A5 of the A chain of human insulin (cf. SEQ ID NO 1),
(A12–A19) are the amino acid residues in the positions A12 to A19 of the A chain of human insulin (cf. SEQ ID NO 1),
(B8–B18) are the amino acid residues in the positions B8 to B18 of the B chain of human insulin (cf. SEQ ID NO 2) and
(B20–B26) are the amino acid residues in the positions B20 to B26 of the B chain of human insulin (cf. SEQ ID NO 2).

Further preferred embodiments of the present invention are crystals containing an insulin analog or a physiologically tolerable salt thereof of the formula I, wherein the amino acid residue in position B1 of the B chain is a phenylalanine residue (Phe) or an insulin analog or a physiologically tolerable salt thereof of the formula I, wherein the amino acid residue in position B3 of the B chain is a histidine (His), lysine (Lys) or arginine (Arg) residue.

Further preferred embodiments of the present invention are crystals comprising an insulin analog or a physiologically tolerable salt thereof of the formula I, wherein at least one of the amino acid residues in the positions B27, B28 and B29 of the B chain is replaced by a naturally occurring amino acid residue which is selected from the group consisting of the neutral or the acidic amino acids, an insulin analog or a physiologically tolerable salt thereof of the formula I, wherein at least one of the amino acid residues in the positions B27, B28 and B29 of the B chain is a naturally occurring amino acid residue which is selected from the group consisting of isoleucine (Ile), aspartic acid (Asp) and glutamic acid (Glu), preferably wherein at least one of the amino acid residues in the positions B27, B28 and B29 of the B chain is replaced by a naturally occurring amino acid residue which is selected from the group consisting of the neutral amino acids, or particularly preferably wherein at least one of the amino acid residues in the positions B27, B28 and B29 of the B chain is an isoleucine residue (Ile), or an insulin analog or a physiologically tolerable salt thereof of the formula I, wherein at least one of the amino acid residues in the positions B27, B28 and B29 of the B chain is a naturally occurring amino acid residue which is selected from the group consisting of the acidic amino acids, preferably wherein at least one of the amino acid residues in the positions B27, B28 and B29 of the B chain is an aspartic acid residue (Asp), preferably wherein the amino acid residue in position B27 or B28 of the B chain is an aspartic acid residue (Asp), or wherein at least one of the amino acid residues in the positions B27, B28 and B29 of the B chain is a glutamic acid residue (Glu).

A preferred embodiment of the present invention are also crystals comprising an insulin analog or a physiologically tolerable salt thereof of the formula I, wherein the amino acid residue in position B29 of the B chain is an aspartic acid residue (Asp).

Further preferred embodiments are crystals comprising an insulin analog or a physiologically tolerable salt thereof of the formula I, wherein the amino acid residue in position B27 of the B chain is a glutamic acid residue (Glu), an insulin analog or a physiologically tolerable salt thereof of the formula I, wherein the amino acid residue in position B28 of the B chain is a glutamic acid residue (Glu), or an insulin analog or a physiologically tolerable salt thereof of the formula I, wherein the amino acid residue in position B29 of the B chain is a glutamic acid residue (Glu).

Very particularly preferred crystals are those comprising an insulin analog or a physiologically tolerable salt thereof, which is distinguished in that the B chain has the sequence
Phe Val Lys Gln His Leu Cys Gly Ser His Leu Val Glu Ala Leu Tyr Leu Val Cys Gly Glu Arg Gly Phe Phe Tyr Thr Pro Glu Thr (SEQ ID NO 6), or an insulin analog or a physiologically tolerable salt thereof, which is distinguished in that the amino acid residue in position B27 of the B chain is an isoleucine residue (Ile), preferably an insulin analog or a physiologically tolerable salt thereof, which is distinguished in that the B chain has the sequence
Phe Val Lys Gln His Leu Cys Gly Ser His Leu Val Glu Ala Leu Tyr Leu Val Cys Gly Glu Arg Gly Phe Phe Tyr Ile Pro Lys Thr (SEQ ID NO 4), or an insulin analog or a physiologically tolerable salt thereof of the formula I, wherein the amino acid residue in position B28 of the B chain is an isoleucine residue (Ile), preferably an insulin analog or a physiologically tolerable salt thereof, which is distinguished in that the B chain has the sequence
Phe Val Lys Gln His Leu Cys Gly Ser His Leu Val Glu Ala Leu Tyr Leu Val Cys Gly Glu Arg Gly Phe Phe Tyr Thr Ile Lys Thr (SEQ ID NO 5).

The insulin analogs of the formula I can preferably be prepared by genetic engineering.

The preparation of the insulin of the formula I is mainly carried out by genetic engineering by means of site-directed mutagenesis according to standard methods.

For this, a gene structure coding for the desired insulin analog of the formula I is constructed and expressed in a host cell—preferably in a bacterium such as *E. coli* or a yeast, in particular *Saccharomyces cerevisiae* and, if the gene structure codes for a fusion protein, the insulin analog of the formula I is released from the fusion protein; analogous methods are described, for example, in EP-A-0 211 299, EP-A-0 227 938, EP-A-0 229 998, EP-A-0 286 956 and DE patent application P 38 21 159.

The removal of the fusion protein portion can be carried out chemically by means of cyanogen halide (see EP-A-0 180 920) after cell disruption.

In the preparation by means of a preproinsulin precursor which possesses a fusion protein portion (presequence) according to U.S. Pat. No. 5,358,857, the removal of the fusion protein portion is carried out at a later stage together with the removal of the C peptide.

The insulin precursor is then subjected to oxidative sulfitolysis according to the method described, for example, by R. C. Marshall and A. S. Inglis in "Practical Protein Chemistry—A Handbook" (editor A. Darbre) 1986, pages 49–53 and then renatured in the presence of a thiol with the formation of the correct disulfide bridges, e.g. according to the method described by G. H. Dixon and A. C. Wardlow in Nature (1960), pages 721–724.

The insulin precursor can, however, also be directly folded (EP-A-0 600 372; EP-A-0 668 292).

The C peptide is removed by means of tryptic cleavage—for example according to the method of Kemmler et al., J. B. C. (1971), pages 6786–6791 and the insulin analog of the formula I is purified by means of known techniques such as chromatography—e.g. EP-A-0 305 760—and crystallization.

In these processes, the B chain C terminal ends with arginine or two arginine residues. These can be removed enzymatically by means of carboxypeptidase B.

The insulin analogs possess full biological activity. This was shown by intravenous administration to rabbits and the lowering of blood glucose resulting therefrom. The more rapid onset of action after subcutaneous administration was shown using the euglycemic clamp technique on fasting dogs (EP 0 885 961 Al, examples 5 and 6). 0.3 lU/kg was administered. The reference preparation was human insulin. In the clamp technique, after the insulin injection, the blood glucose value is measured at brief time intervals and exactly enough glucose is infused in order to compensate the lowering. This has the advantage that no counterregulation occurs in the animals, as would be the case with a large decrease in the blood glucose after the administration of insulin. The amount and the variation with time of the infused glucose characterize the action of the insulin. Lys (B3), Glu(B29)-(SEQ ID NO 6) and Lys(B3), Ile(B28)-(SEQ ID NO 4) insulin have a markedly more rapid onset of action than human insulin. The maximum action (glucose infusion rate) is achieved after 100 minutes with human insulin, but after 80 minutes with Lys (B3), Glu (B29)-insulin (SEQ ID NO 6) and as early as after 60 minutes with Lys (B3), Ile(B28)-insulin (SEQ ID NO 4). These analogs, if they are injected shortly before a meal, should therefore compensate the postprandial increase in the blood glucose better than human insulin.

The insulin analogs described are suitable both for the therapy of type I and type II diabetes mellitus, preferably in combination with a basal insulin.

The insulin analogs can be employed in the pharmaceutical preparations also in the form of their physiologically tolerable salts, as alkali metal or as ammonium salts. An arbitrary amount of one or more insulin analogs of the formula I or an insulin analog of the formula I can be present in a mixture of further of these insulin analogs independently of one another in each case in dissolved, amorphous and/or crystalline form.

Insulins and insulin analogs are often prepared as aqueous pharmaceutical formulations which contain zinc ions.

The addition of zinc ions to insulin preparations is essentially carried out for two reasons:
1. $Zn^{2+}$ ions have a stabilizing action on insulin preparations since these promote the formation of insulin hexamers [Brange et al. *Diabetic Medicine*, 3, 532–536 (1986).
2. Depending on the $Zn^{2+}$ ion concentration, the variation with time of the influx and efflux kinetics of insulin preparations can be controlled.

In the case of rapidly acting insulins, points 1 and 2 lead to problems. On account of the increased pharmaceutical stability of the preparation, high concentrations of insulin hexamers are advantageous. Since $Zn^{2+}$ ions, however, delay the influx and efflux kinetics of the insulin analog, they act contrary to the desired kinetics of the active compound release. It has therefore been decided to prepare one of the insulin analogs described, namely Lys B3, Glu B29 human insulin, in the form of a zinc-free, aqueous solution (International patent application PCT/EP02/02625).

For the preparation of the zinc-free, aqueous formulation of the insulin analogs described, in particular Lys B3, Glu B29 human insulin, there is the need to be able to employ zinc-free crystals of the insulin analogs. Moreover, zinc-free crystals of the insulin analogs according to the invention can also be used for the preparation of other pharmaceutical formulations, e.g. in the case of solid formulations or emulsions for administration by inhaler, or in the case of oral administration.

All references cited herein are hereby incorporated in their entirety by reference.

The object on which the invention is based was thus the preparation of zinc-free crystals of the insulin analogs described. At the same time, replacement of zinc ions by other divalent ions, which are unsuitable for pharmaceutical formulations on account of their toxicity, should also be avoided.

It has now surprisingly been found that the insulin analogs described can be prepared in hexamer crystals which contain no divalent ions such as, for example, zinc ions. This may be illustrated in greater detail by example of the insulin analog Lys B3, Glu B29-human insulin.

This novel crystal form of Lys B3, Glu B29-human insulin is crystallographically isomorphous to the classical 2Zn insulin type which is described in the literature for porcine insulin and human insulin [Baker et al., *Phil. Trans. Roy Soc.* 319, 369–454 (1988)]. The novel zinc-free hexamer crystals belong to the rhombohedral space group R3 (No. 146) with two insulin monomers per asymmetric unit. The elemental cell axes at −70° C. (by use of the shock freezing method) were determined to be: A=81.5 Å, C=33.3 Å. The X-ray structural analysis of the novel crystal form at 1.8 Å showed that instead of the $Zn^{2+}$ ions (in the classical 2Zn type) having bonding distances ($Zn^{2+}$-His-B10) of around 2.0 Å, in the novel crystal form of Lys B3, Glu B29-human insulin only a very small electron density peak is found which corresponds to a water molecule ($H_2O$) (bonding distance $H_2O$ -His-B10 around 2.3 Å). Both the quantity of the electron density and the bonding distance show for an insulin having a glutamate B21 side chain a hitherto unknown structural arrangement of the region around the histidine B10 side chain.

The (1σ-2Fo-Fc) electronic density of the region around histidine B-10 is significantly different to the classical 2Zn type, in which a $Zn^{2+}$ ion are coordinated octahedrally by three symmetry-adjacent histindine-B10 each and 3 water molecules each. The bonding distances ($Zn^{2+}$-His-B10) of the structures of the 2Zn type deposited in the PDB databank [Bernstein et al; *J.Mol.Biol.* 112, 535–542 (1977)] are between 1.9 and 2.1 Å and are significantly different to the observed bonding distances of around 2.3 Å in the novel, zinc-free crystal structure. What is special about the novel hexamer crystal form of Lys B3, Glu B29-human insulin described here is that it contains insulin hexamers without the divalent cations (e.g. $Zn^{2+}$, $Co^{2+}$, $Cd^{2+}$) otherwise necessary for this. Previously, it has been assumed that the formation of insulin hexamers without divalent cations is only possible if the repulsive forces of the glutamate B21 side chain can be reduced by protein engineering (e.g. by the replacement of B21-Glu by Gln) [Bentley et al., *J.Mol.Biol.* 228, 1163–1176 (1992)]. The retention of the Glu-B21 side chain—which promotes the decomposition of insulin hexamers—is, however, especially important for rapidly acting insulins for the retention of rapid influx and efflux kinetics.

The invention accordingly relates to crystals of an insulin analog, in which asparagine (Asn) in position B3 of the B chain is replaced by a naturally occurring basic amino acid residue and at least one amino acid residue in the positions B27, B28 or B29 of the B chain is replaced by another naturally occurring neutral or acidic amino acid residue, where phenylalanine (Phe) in position B1 of the B chain can optionally be absent, the crystal being present in the space group R3 (No. 146) with the cell axes A=81.5 Å±1 Å; in particular the molecules of the insulin analog being present in the form of zinc-free hexamers, consisting of in each case three dimers.

A further subject of the invention are crystals as described above, where the histidine B10 residues of in each case three molecules of the insulin analog in a hexamer are bonded to a water molecule, a dihydrogenphosphate ion ($H_2PO_4^-$), a monohydrogenphosphate ion ($HPO_4^{2-}$) or a sulfate ion ($SO_4^{2-}$) via hydrogen bonds.

A further subject of the invention are crystals as described above, where the histidine B10 residues of the molecules of the insulin analog in a hexamer are in each case folded back onto their own dimer and no hydrogen bond formation of the histidine B10 residues to a water molecule is present.

The crystals according to the invention in this case contain insulin analogs according to the formula I described above, where in particular the amino acid residue in position B3 of the B chain of the insulin analog is a histidine (His), lysine (Lys) or arginine (Arg) residue; and where particularly preferably at least one of the amino acid residues in the positions B27, B28 and B29 of the B chain is a naturally occurring amino acid residue which is selected from the group consisting of isoleucine (Ile), aspartic acid (Asp) and glutamic acid (Glu).

The crystals according to the invention in this case in particular contain an insulin analog wherein the B chain has the sequence Phe Val Lys Gln His Leu Cys Gly Ser His Leu Val Glu Ala Leu Tyr Leu Val Cys Gly Glu Arg Gly Phe Tyr Pro Thr (SEQ ID NO 6).

A further subject of the invention is a pharmaceutical preparation which contains at least one crystal such as described above, where preferably an excipient can be present which facilitates the absorption of the insulin analog into the blood and very particularly preferably where the pharmaceutical formulation has an insulin activity having a rapid onset of action.

A further subject of the invention is a pharmaceutical preparation which contains at least one crystal as described above and an excipient, which is used in inhalative and/or oral formulations of insulin or insulin analogs.

A further subject of the invention is a process for the preparation of a crystal as described above, in which
(a) a zinc-free, amorphous powder of an insulin analog as described above is dissolved in water in a concentration of 15–25 mg/ml,
(b) precipitation using a suitable precipitant is carried out, and
(c) the crystals are isolated and dried;

the insulin analog in particular being Lys B3, Glu B29-human insulin.

A further subject of the invention is a process for the preparation of a crystal as described above, in which the precipitant is selected from a group comprising
(a) ammonium dihydrogenphosphate,
(b) a combination of ammonium dihydrogenphosphate and trisodium citrate; and
(c) a combination of ammonium sulfate and polyethylene glycol of various molecular weights;

the precipitant preferably used being ammonium dihydrogenphosphate or diammonium hydrogenphosphate at pHs between 3.0 and 8.0, or ammonium dihydrogenphosphate/diammonium hydrogenphosphate in combination with trisodium citrate at a pH of 5.5±1.5 or ammonium sulfate in combination with PEG of various molecular weights at a pH of 6.0±1.5.

The invention also relates to the use of a crystal such as described above for the production of a pharmaceutical for the treatment of diabetes of types I and/or II.

The invention also relates to a method of treating Type I or Type II diabetes comprising administering to a patient in need thereof a therapeutically effective amount of one or more crystals as described above.

As used herein, the following definitions apply:
"Patient" means a warm blooded animal, such as for example rat, mice, dogs, cats, guinea pigs, and primates such as humans.
"Treat" or "treating" means to alleviate symptoms, eliminate the causation of the symptoms either on a temporary or permanent basis, or to prevent or slow the appearance of symptoms of the named disorder or condition.
"Therapeutically effective amount" means a quantity of the compound which is effective in treating the named disorder or condition.

The invention is illustrated in greater detail by means of the examples, without being restricted thereto.

The above disclosure generally describes the present invention. A more complete understanding can be obtained by reference to the following specific examples which are provided herein for purposes of illustration only, and are not intended to limit the scope of the invention.

EXAMPLE 1

Preparation of the Novel Zinc-Free Hexamer Crystal Form:
Amorphous, zinc-free powder of Lys B3, Glu B29-human insulin is dissolved in unbuffered form in dist. water/HCl at pH around 2.0. This process allows the formation of a clear solution at insulin concentrations of around 20 mg/ml. The crystallization is carried out in 24-well Linbro plates according to the hanging-drop method. The precipitant used is the following reagent of the "Protein Crystallization Screening Kit" of Hampton Research Inc.: 1. 0.4 M ammonium dihydrogenphosphate, pH 4.2.

EXAMPLE 2

Preparation of the Novel Zinc-Free Hexamer Crystal Form
Amorphous, zinc-free powder of Lys B3, Glu B29-human insulin is dissolved in unbuffered form in dist. water/HCl at pH around 2.0. This process allows the formation of a clear solution at insulin concentrations of around 20 mg/ml. The crystallization is carried out in 24-well Linbro plates according to the hanging-drop method. The precipitant used is the following reagent of the "Protein Crystallization Screening Kit" of Hampton Research Inc.: 1 M ammonium dihydrogenphosphate, 0.1 M trisodium citrate, pH 5.6.

EXAMPLE 3

Preparation of the Novel Zinc-Free Hexamer Crystal Form
Amorphous, zinc-free powder of Lys B3, Glu B29-human insulin is dissolved in unbuffered form in dist. water/HCl at pH around 2.0. This process allows the formation of a clear solution at insulin concentrations of around 20 mg/ml. The crystallization is carried out in 24-well Linbro plates according to the hanging-drop method. The precipitant used is the following reagent of the "Protein Crystallization Screening Kit" of Hampton Research Inc.: 0.2 M ammonium sulfate, 20% of PEG 3350, pH 6.0.

EXAMPLE 4

X-Ray Structural Analysis
The crystals obtained according to examples 1–3 are well ordered and make possible an X-ray structural analysis, which for an insulin having a glutamate B21 side chain shows a hitherto unknown structural arrangement of the region around the histidine B10 side chain.

Zinc-containing human insulin crystals of the 2Zn type have, as a space group, R3 (146) and cell axes of A=82.5, C=34.0 Å. Zinc-free crystals of compound I are isoamorphous and typically have cell axes of A=81.5, C=33.3 Å. The insulin molecules in the zinc-containing crystal structure of human insulin and the zinc-free crystal structure of Lys B3, Glu B29-human insulin folded in the $T_6$ or 2Zn type. In the 2Zn insulin ($T_6$), all 6 monomers are present in the "T=tensed" state. The N terminus of the B chains is extended without a significant secondary structural feature; no α-helix secondary structure is present as in the alternative R state. Significant differences in the crystal structures of human insulin and compound I result in the arrangement of the region around the histidine B10 side chain.

For all preparation methods according to examples 1–3, high-resolution single-crystal X-ray structural analyses are available which prove the zinc-free state of these insulin hexamer crystals. The elemental cell axes and crystal symmetry determined were:
Preparation process 1: A=81.52, C=33.31 Å, R3 (space group No. 146)
Preparation process 2: A=81.51, C=33.43 Å, R3 (space group No. 146)
Preparation process 3: A=81.38, C=33.22 Å, R3 (space group No. 146).

I claim:

1. A crystal of a human insulin analog, wherein said analog consists of the human insulin sequence except that asparagine (Asn) in position B3 of the B chain is replaced by lysine (Lys) and lysine (Lys) in position B29 of the B chain is replaced by glutamic acid (Glu), the crystals being present in space group R3 (No. 146) with unit cell dimensions a=81.5±1.0 Å and c=33.3±1.0 Å.

2. The crystal of claim 1, wherein the molecules of the insulin analog are present in the form of the zinc-free hexamers consisting of in each case three dimers.

3. The crystal of claim 2, wherein the histidine B10 residues of in each case three molecules of the insulin analog in a hexamer are bonded to a water molecule via hydrogen bonds.

4. The crystal of claim 2, wherein the histidine B10 residues of in each case three molecules of the insulin analog in a hexamer are bonded to a dihydrogenphosphate ion ($H_2PO_4^-$) via hydrogen bonds.

5. The crystal of claim 2, wherein the histidine B10 residues of in each case three molecules of the insulin analog in a hexamer are bonded to a monohydrogenphosphate ion ($HPO_4^{2-}$) via hydrogen bonds.

6. The crystal of claim 2, wherein the histidine B10 residues of in each case three molecules of the insulin analog in a hexamer are bonded to a sulfate ion ($SO_4^{2-}$) via hydrogen bonds.

7. The crystal of claim 1, wherein the histidine B10 residues of the molecules of the insulin analog in a hexamer are in each case folded back onto their own dimer and no hydrogen bond formation of the histidine B 10 residues to a water molecule is present.

8. The crystal of claim 1, wherein the insulin analog is further characterized as a compound of formula I, (B20–B26) are the amino acid residues in the positions B20 to B26 of the B chain of human insulin, (B30) is the amino acid residue in position B30 of the B chain of human insulin, B1 is a phenylalanine residue (Phe), B3 is a lysine residue (Lys), B27, B28 are the amino acid residues in the positions B27 to B28 of the B chain of human insulin, and B29 is glutamic acid (Glu).

9. A pharmaceutical preparation comprising at least one crystal of claim 1.

10. The pharmaceutical preparation of claim 9 further comprising an excipient which facilitates the absorption of the insulin analog into the blood.

11. The pharmaceutical preparation of claim 9 further comprising an excipient, which is used in inhalative and/or oral formulations of insulin or insulin analogs.

12. A process for the preparation of one or more crystal of claims 1 comprising the steps of:

a) dissolving a zinc-free, amorphous powder of the insulin analog of claim 1 in a suitable liquid to a concentration of 15–25 mg/ml;

b) precipitating the crystal using a suitable precipitant selected from:

i) ammonium dihydrogenphosphate or diammonium hydrogenphosphate in combination with trisodium citrate at pH 5.5±1.5, or

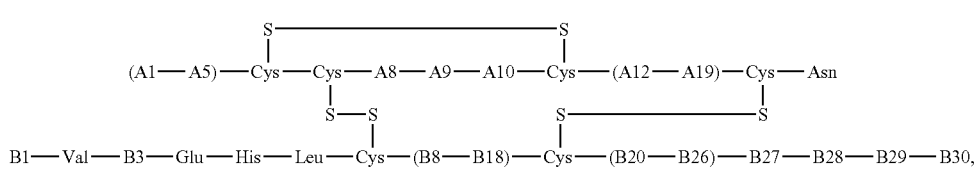

I in which (A1–A5) are the amino acid residues in the positions A1 to A5 of the A chain of human insulin (A8–A10) are the amino acid residues in the positions A8, A9 and A10 of the A chain of human insulin, (A12–A19) are the amino acid residues in the positions A12 to A19 of the A chain of human insulin, (B8–B18) are the amino acid residues in the positions B8 to B18 of the B chain of human insulin, ii) ammonium sulfate in combination with polyethylene glycol of various molecular weights at pH 6.0±1.5; and c) isolating and drying said crystals.

13. A method of treating Type I or Type II diabetes comprising administering to a patient in need thereof a therapeutically effective amount of one or more crystals of claim 1.

* * * * *

SEQUENCE LISTING

<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
 1               5                  10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Version of
      b-chain

<400> SEQUENCE: 3

Phe Val Asn Gln His Leu Cys Phe Val Lys Gln His Leu Cys Gly Ser
 1               5                  10                  15

His Leu Val Glu Ala Leu Tyr Leu Val Cys Gly Glu Arg Gly Phe Phe
            20                  25                  30

Tyr Thr Pro Glu Thr
        35

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Version of
      b-chain

<400> SEQUENCE: 4

Phe Val Lys Gln His Leu Cys Gly Ser His Leu Val Glu Ala Leu Tyr
 1               5                  10                  15

Leu Val Cys Gly Glu Arg Gly Phe Phe Tyr Ile Pro Lys Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Version of
      b-chain

```
<400> SEQUENCE: 5

Phe Val Lys Gln His Leu Cys Gly Ser His Leu Val Glu Ala Leu Tyr
 1               5                  10                  15

Leu Val Cys Gly Glu Arg Gly Phe Phe Tyr Thr Ile Lys Thr
                20                  25                  30
```